United States Patent [19]

Zehner

[11] 4,005,129
[45] Jan. 25, 1977

[54] PROCESS FOR THE OXIDATIVE CARBONYLATION OF ALCOHOLS AND METHOD FOR THE REOXIDATION OF REDUCED COPPER SALTS PRODUCED BY THE OXIDATION CARBONYLATION

[75] Inventor: Lee R. Zehner, Media, Pa.
[73] Assignee: Atlantic Richfield Company, Los Angeles, Calif.
[22] Filed: June 4, 1975
[21] Appl. No.: 583,810
[52] U.S. Cl. .................. 260/485 R; 260/465 D; 260/465.4; 260/485 H; 260/485 L; 260/485 J; 260/485 P
[51] Int. Cl.$^2$ .................................... C07C 69/36
[58] Field of Search ....... 260/485 R, 485 H, 485 L, 260/485 J, 485 P, 465 D, 465.4
[56] References Cited
UNITED STATES PATENTS 3,393,136   7/1968   Fenton et al. ............. 260/485 R

FOREIGN PATENTS OR APPLICATIONS 2,213,435   10/1973   Germany .................. 260/485 R

*Primary Examiner*—Jane S. Myers
*Attorney, Agent, or Firm*—Delbert E. McCaslin

[57] ABSTRACT

A process for the oxidative carbonylation of alcohols with carbon monoxide using metal salt catalysts, an amine base, amine salts, and copper (II) oxidizing salts to produce a predominate amount of oxalate ester and the reoxidation of the reduced copper (II) oxidizing salts with an oxygen-containing gas under mild conditions in the presence of the amine salt. After removal of water by physical or chemical means the oxidative carbonylation reaction can be repeated without any loss of yield of the oxalate ester.

22 Claims, No Drawings

PROCESS FOR THE OXIDATIVE CARBONYLATION OF ALCOHOLS AND METHOD FOR THE REOXIDATION OF REDUCED COPPER SALTS PRODUCED BY THE OXIDATION CARBONYLATION

BACKGROUND OF THE INVENTION

In co-pending application of Lee R. Zehner et al, Ser. No. 564,242, filed Apr. 2, 1975, entitled PROCESS FOR THE PREPARATION OF OXALATE ESTERS and incorporated herein by reference, there is disclosed a process for the oxidative carbonylation of alcohols at elevated temperatures and pressures in the presence of palladium (II), rhodium (III), platinum (II) and copper (I) or (II) catalysts and a stoichiometric amount of a copper (II) or iron (III) oxalate, sulfate, acetate or trifluroacetate oxidant salts and an aliphatic, aromatic or heterocyclic amine or ammonia to produce a predominant amount of the desired oxalate ester. Various counterions and ligands of the metal catalysts may also be employed.

The present invention is directed to an improved process for the oxidative carbonylation of alcohols, as disclosed in the above described co-pending application, wherein an amine salt is added to the reaction mixture or formed in situ in the reaction mixture by the addition of an acid as sulfuric acid or acetic acid, so that the reduced form of the stoichiometric copper (II) oxidizing salt resulting from the oxidative carbonylation can be reoxidized with oxygen or oxygen-containing gas and under mild conditions. By this process the synthesis of oxalate esters can be carried out as a cyclic process providing high yield of the oxalate esters and exceeding the yield of carbonates.

The addition of excess amine salts to the reduced form of the copper (II) oxidizing salt resulting from the oxidative carbonylation allows the reoxidation (oxygen-oxidation) to take place without precipitation of basic copper salts. The basic copper salts were shown to be insoluble in the reaction solvents and therefore to be ineffective oxidants for the oxidative carbonylation. In the presence of the additional amine salt, the reoxidation coproduct, water, can be removed, for example by chemical reaction or by azeotropic distillation. Without the excess amine salt, the overall synthesis of oxalate esters cannot be accomplished in a cyclic manner.

U.S. Pat. No. 3,114,762 discloses a method for the preparation of alkyl carbonates by reacting carbon monoxide with an alcohol in the presence of platinum or palladium chloride and in the added presence of an oxidizing salt for reoxidizing the catalyst in situ. The reaction is carried out at temperatures of from 20° C. to 100° C. and carbon monoxide pressures of 1 to 500 atmospheres. Runs carried out for comparison even at higher temperatures only resulted in trace amounts of the oxalate.

U.S. Pat. No. 3,393,136 describes a process for the preparation of oxalates by contacting carbon monoxide at superatmospheric pressure, with a saturated monohydric alcohol solution of a platinum group metal salt and a soluble ferric or cupric salt (redox agent) while maintaining the salts in a highly oxidized state by the simultaneous introduction of oxygen or the application of a direct current electrical potential to the reaction zone. When oxygen is employed, explosive mixtures of oxygen and combustible organic vapors in the gas phase must be avoided and water scavengers or dehydrating agents such as alkyl orthoformic acid esters must be added to the liquid phase to prevent the accumulation of water.

In a recent article by Donald M. Fenton and Paul J. Steinwand, Journal of Organic Chemistry, Vol. 39, No. 5, 1974, pp. 701–704, a general mechanism for the oxidative carbonylation of alcohols to yield dialkyl oxalates using a palladium redox system, oxygen and dehydrating agents has been proposed. In the absence of the necessary dehydrating agent, a large amount of carbon dioxide is formed and oxalates are not produced. The necessity of the iron or copper redox system during the oxalate synthesis is emphasized.

A recent West German Pat. No. 2,213,435 discloses a method for the synthesis of oxalic acid and oxalate esters in water and alcohol respectively. A platinum group metal salt, a salt of a metal more electropositive than the platinum group metal, e.g. copper (II) chloride and an alkali metal salt comprise the catalyst. Oxygen in stoichiometric amounts was employed as the oxidant. A disadvantage of such reaction is that explosive mixtures of oxygen and carbon monoxide are necessary to effect reaction. Under non-explosive conditions only trace amounts of oxalate can be obtained.

Many important commercial applications have been developed for the oxalate products of this invention, for example, as cellulose ether or ester and resin solvents, as dye intermediates and the preparation of pharmaceuticals.

The process of the present invention provides a means of carrying out the oxidative carbonylation of alcohols as a cyclic process with the reoxidation of reduced copper (II) oxidant salts and thus obtain high yield selectivity to the oxalate esters. Carbonates esters and carbon dioxide associated with such reactions are minimized by a critical regulation of the amine catalyst, and oxidant anions and by maintaining the reaction mixture substantially anhydrous.

Other advantages of the present invention, as compared to known prior art processes are (1) elimination of hazardous operational conditions by avoiding explosive mixtures of oxygen and carbon monoxide, (2) avoiding any necessity for using dehydrating agents as no water is formed as a result of the instant oxidative carbonylation process; when air or $O_2$ is used as the oxidant water and $CO_2$ are formed and the presence of water always decreases the yield of oxalate and increases the $CO_2$, (3) avoiding the use of large amounts of corrosive chloride ions, (4) ease of recovery and reoxidation of the metal salts in a stream of air or oxygen for reuse in the oxidative carbonylation process and (5) the ability to employ in the process as catalysts the more readily available copper salts in place of the more expensive platinum group metal salts.

SUMMARY OF THE INVENTION

According to the present invention there is provided a much improved oxidative carbonylation process for the preparation in high yield of oxalates by reacting carbon monoxide with an alcohol which process is carried out at elevated temperatures and pressures in the presence of a metal salt catalyst, copper (II) oxidant salts, amines, and an excess of amine salts and under relatively anhydrous conditions.

It has been found that the above-mentioned reaction can be carried out at high conversions to the oxalate ester, over the carbonate which may be present in only trace amounts, by conducting the reaction in the presence of at least a stoichiometric quantity of an amine, stoichiometric quantities of copper (II) oxidizing salts and an excess of amine salts to provide a pronounced effect on oxalate ester selectivity. In addition, it has been found that alternatively catalytic amounts of various ligands, which will not work in themselves, may be used as co-catalysts in conjunction with the metal salt catalysts, the amines, the amine salts and the oxidant salts.

It is a primary object of this invention to provide a process for the preparation of oxalate esters by a cyclic process and in high yield while avoiding operational problems associated with prior processes.

It is another object of this invention to provide a novel reaction system useful in the conversions of carbon monoxide and alcohol to oxalate esters and a method for reoxidation of reduced copper (II) oxidant salts for reuse in the reaction system. It is a further object of this invention to provide a specific mechanism for the employment of catalysts, oxidant, amine salts and an amine in an oxidative carbonylation process.

A further object is to provide an improved process for the preparation of commercially important diethyl or diisopropyl oxalate in high yield.

These and other objects and advantages of this invention will be come apparent from the description of the invention which follows and from the claims.

DESCRIPTION OF THE INVENTION

In accordance with this invention, an oxalate ester is produced by reacting, under relatively anhydrous liquid phase conditions, an alcohol with carbon monoxide at elevated temperatures and pressures in the presence of a catalyst comprising a palladium, rhodium, platinum or copper salt, with or without a ligand as a co-catalyst, and at least a stoichiometric amount of an amine and in the presence of a stoichiometric amount of a copper (II) metal oxidant salt, along with an excess of an amine salt such as triethylammonium sulfate. The synthesis of the oxalate esters can be carried out as a cyclic process according to the following postulated equations:

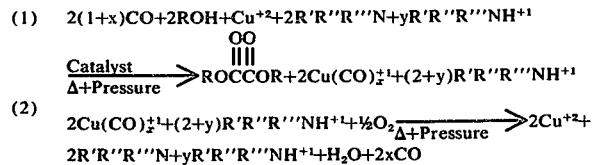

wherein R is selected from monohydric substituted or unsubstituted aliphatic, alicyclic or aromatic groups, R', R" and R''' may be hydrogen, or a substituted or unsubstituted aliphatic, aromatic, cycloaliphatic or heterocyclic group, $x$ is less than or equal to one and $y$ is greater than zero. In the reaction the amine, employed in at least a stoichiometric amount, functions as a hydrogen ion acceptor.

As indicated above, the amine salt may be formed in situ in the reaction mixture by the addition of an acid, in which case, the amine must be employed in excess of the stoichiometric amount in the reaction mixture in order to form the necessary quantity of amine salt. Thus, triethylamine can, for example, be initially employed in amounts greater than stoichiometric and sulfuric acid added to form triethylammonium sulfate in the desired quantities.

The reaction between the alcohol, carbon monoxide, amine and oxidant may be carried out in an autoclave or any other high pressure reactor. A general procedure is to charge the alcohol, amine, amine salt (or the required amount of amine and acid), catalyst, and the oxidant into the reactor vessel, introduce the proper amount of carbon monoxide to obtain the desired reaction pressure and then heat the mixture to the desired temperature for the appropriate period. The reaction can be carried out batchwise or as a continuous process and the order of addition of the reactants may be varied to suit the particular apparatus employed. The reaction products are recovered and treated by any conventional method such as distillation and/or filtration, etc. to effect separation of the oxalate from unreacted materials, catalyst, oxidant, amine salts, by-products, etc.

The reaction is performed and takes place under relatively anhydrous conditions, i.e., in an essentially anhydrous alcoholic media. The alcohols suitable for use in the process of the present invention can be monohydric saturated aliphatic and alicyclic alcohols or aromatic alcohols and may contain other substituents such as halo, amido, alkoxy, amino, carboxy, cyano, etc. radicals in addition to the hydroxyl group. The substituents, in general, do not interfere with the reaction of the invention.

The alcohols which may be primary, secondary or tertiary alcohols conform to the general formula ROH, wherein R is an optionally substituted aliphatic or alicyclic group preferably containing from 1 to 20 carbon atoms. R may also be an aromatic group containing one or more benzenoid rings perferably not more than 3 rings which may be fused or joined by single valency bonds, directly or through bridging groups which may be, for example, oxygen or sulfur atoms or sulfoxide sulfone or carbonyl groups or alkylene groups in which, if desired, the carbon chain may be interrupted by, for example, oxygen or sulfur atoms, sulfoxide, sulfone or carbonyl groups, for example methylene, oxymethylene, dimethylene sulfone or dimethylene ketone groups. Representative alcohols especially suitable for use in this invention are monohydric alcohols such as methyl, ethyl, n-, iso-, sec-, and tert-butyl, amyl, hexyl, octyl, lauryl, n- and iso-propyl, cetyl, benzyl, chlorobenzyl and methoxy-benzyl alcohols as well as, for example cyclohexanol, octanols, heptanols, decanols, undecanols, 2 ethyl hexanol, nonanol, myristyl alcohol, stearyl alcohol, methyl cyclohexanol, pentadecanol, oleyl and eicosonyl alcohols, and the like. The preferred alcohols are the primary and secondary monohydric alcohols, such as ethanol and 2-propanol.

The amines employed in the process of the invention which may be ammonia or primary, secondary or tertiary amines include aliphatic, cycloaliphatic, aromatic and heterocyclic amines or mixtures thereof. The amines may be unsubstituted or contain other substituents such as halides, alkyl, aryl, hydroxy, amino, alkylamino, carboxy, etc.

Representative amines, as hereinabove described, include for example, mono-, di- and tri-methyl, ethyl, and propyl amines, iso- and diiso-propyl amines, allyl amines, mono-, di-, tri-, iso and diisobutyl amines, 1-methylpropyl amine, 1,1-dimethyl-ethyl amine, amyl amines, cyclohexyl amine, dicyclohexylamine, 1,3-dimethyl-butyl amine, 2-ethylhexylamine, 1-cyclopentyl-2-aminopropane, 1,1,3,3-tetramethylbutylamine, aniline, ethylene diamine, methylene diamines, ethanolamines, octylamines, n-decylamine, do-, tetra-, hexa-, octa-, dido-, ditetra-, diocta-, trido- and trioctadecyl amines, aniline, chloroanilines, nitroanilines, toluidines, naphthylamines, N-methyl and N-ethyl, and N,N-dimethyl and N,N-diethyl aniline, di- and triphenylamines, N,N-diamylaniline, benzyl dimethyl amine, piperidine, pyrrolidine, etc. The preferred amines are the tertiary amines such as triethylamine and ammonia.

The metal salt catalysts which may be employed in the process of this invention are the palladium (II), platinum (II), rhodium (III), copper (II) or copper (I) salts. Among the chemical forms of the metal compounds which can be used are the palladium, platinum and rhodium, halides, sulfates, oxalates and acetates and the copper halides preferably the palladium (II) and copper (I) or (II) halides such as palladium (II) chloride palladium (II) iodide, copper (II) chloride and copper (I) iodide. Representative catalytic metal salt compounds include, for example, palladium (II) chloride, copper (II) chloride, rhodium (III) chloride, copper (II) iodide, palladium (II) sulfate, palladium (II) oxalate, palladium (II) acetate, palladium (II) iodide, rhodium (III) bromide, platinum (II) chloride, platinum (II) sulfate, etc.

The catalysts employed may be in a homogeneous state in the reaction mixture at reaction conditions. Thus, the catalysts may be present in solution, or suspension and may also be on support materials such as alumina, silica gel, activated carbon or zeolites.

The reaction is generally carried out in the presence of a catalytic proportion of the metal salt catalyst and will proceed with small amounts of the metal salt catalyst compounds herein above described. Generally the proportions of the metal salt catalyst used in the reaction will be equivalent to between about 0.001 to 5 weight per cent of the alcohol employed and are preferably employed in amounts between about 0.01 to 2 per cent by weight of the alcohol employed. Larger or smaller amounts may be employed at varied pressures of reaction rates.

As mentioned hereinabove, a ligand or co-ordination complex compound of the metal catalyst may be employed in the process of the invention as a co-catalyst and thereby also achieve a pronounced increase in the selectivity for the oxalate ester. The ligands may be, for example, alkyl or aryl phosphines, arsines, iodides or stibines. The complexes of the metal catalysts which are suitable as co-catalysts in the process of the present invention include complex compounds of palladium, platinum, rhodium and copper. The complex compounds may contain one or more atoms of the said metals in the molecule and when more than one such atom is present, the metals may be the same or different. The mono- or poly-dentate ligands which are present in the molecule of the complex compounds and in which at least one of the electron-donating atoms is an atom of phosphorous, arsenic or antimony or an iodide ion containing a lone pair of electrons may be, for example, organo-phosphines, -iodides, -arsines and -stibines. Suitable mono-dentate ligands include alkyl phosphines such as trimethylphosphine and tributylphosphine, aryl-phosphines such as triphenylphosphine, mixed alkylaryl phosphines such as diethylphenyl-phosphine and radicals derived from such phosphines, for example the radical having the formula —$P(CH_3)_2$. Hydrocarbyloxy phosphines, i.e., phosphites, such as triphenyl phosphite may also be employed. Suitable polydentate ligands include tetramethyl diphosphinoethane and tetraphenyl diphosphinoethane. Exactly analogous derivatives of arsenic and antimony may be used; however, because of their greater ease of preparation and stability of the derived complexes, the hydrocarbyl derivatives of phosphorus are preferred. It is also preferred to employ alkaline metal iodides, e.g. lithium iodide.

The complex compounds suitable for use in the process of the present invention may contain in the molecule, in addition to the ligands discussed above, one or more other atoms, groups or molecules, which are chemically bonded to the metal atom or atoms. Atoms which may be bonded to the metal include, for example, hydrogen, nitrogen and halogen atoms; groups which may be bonded to the metal include, for example hydrocarbyl, hydrocarbyloxy, carbonyl, nitrosyl, cyano and $SnCl_3$— groups; molecules which may be bonded to the metal include, for example, organic isocyanides and isothiocyanates.

Examples of suitable complex compounds are those represented by the following formulae:

$RhBr_3(PPhEt_2)_3$     $Rh(CO)Cl(AsEt_3)_2$
$RhCl(CO)(PPhEt_2)_2$     $RhCl(CO)(PEt_3)_2$
$Rh(Ph_2PCH_2CH_2PPh_2)_2Cl$     $PdCl_2(PPh_3)_2$
$Rh[(PhO)_3P]_3Cl$
$PdI_2(PPh_3)_2$     $Li_2PdI_4$
$PtCl_2(p-ClC_6H_4Pn—Bu_2)_2$

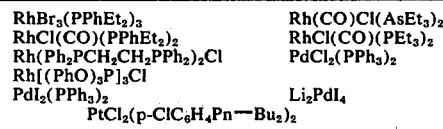

The complex compounds employed may be introduced into the reaction mixture as such, or they may be formed in situ from a suitable metal compound noted above and the desired ligand.

The complex compounds may be used in catalytic amounts of from 0.001 to 5 per cent preferably from 0.01 to 2 per cent by weight of the alcohol to be reacted although larger or smaller amounts may be employed at varied pressures or reaction rates.

The oxidizing salts which are employed in an anhydrous condition and in stoichiometric amounts in the process of the invention include the copper (II) salts such as the sulfates, trifluroacetates, oxalates, or acetates preferably the copper (II) sulfates and trifluoroacetates. Representative oxidant salts include, for example, copper (II) sulfate, copper (II) trifluroacetate, copper (II) acetate and copper (II) oxalate. Unsuitable for use as oxidants in the present invention are the redox metal chlorides, i.e., the ferric or cupric chlorides which form the metal catalyst redox oxidant system. The redox metal chloride salts system is not operative in the method of the present invention. Excess chlorides are detrimental to the reaction system of the present invention.

The amine salts which are employed in an anhydrous condition and in excess, (an excess of amine salt over that normally formed in the carbonylation reaction from the quantity of amine base employed) in the process of the invention include, for example, the ammonium and substituted ammonium sulfates, trifluoroacetates, and acetates, preferably the tertiary amine sulfates such as triethylammonium sulfate. Representative amine salts include, for example diethylammonium sulfate, ethylammonium sulfate, butylammonium sulfate, ammonium sulfate, trimethylammonium sulfate, mono-methylammonium sulfate, trimethyl ammonium hydrogen sulfate, ammonium acetate, ammonium trifluoroacetate, methyl-, ethyl- and butyltrifluoroacetate, etc.

While smaller or larger amounts of the amine salts may be used in the reaction in order to obtain an excess, the salts are generally employed in molar concentrations of from about .25 moles to 2 moles of the salt relative to the stoichiometric amount of amine base employed and may be added as such or formed in situ in such amounts upon the addition of an acid, such as, sulfuric, benzene sulfonic, phosphoric, o-boric, p-toluene sulfonic, acetic or trifluoroacetic, to the reaction mixture while using greater than the stoichiometric quantities of the amine base. The acids which may be used to form the salt include those which do not form a complex with the metal salt catalyst or metal salt oxidant compounds inactivating the catalyst and oxidant. The acids must be of sufficient strength, i.e., stronger than water, and such that the anion will not complex with the metal catalyst or oxidant salt. The salts which may be formed in situ may in themselves not necessarily be isoable and may exist in equilibrium in the reaction mixture under carbonylation and reoxidation reaction conditions. Thus, such salts could not be added per se but, as indicated above may be formed in situ upon the addition of a suitable acid to the reaction mixture containing amine.

The process of the invention can be operated entirely under the liquid phase conditions of the anhydrous alcohol and amine and amine salt. Although not required, solvents, if desired, which are chemically inert to the components of the reaction system may be employed. Suitable solvents include, for example, organic esters such as ethyl acetate, n-propyl formate, isopropyl acetate, sec- and iso-butyl acetate, amyl acetate, cyclohexyl acetate, n-propyl benzoate, lower alkyl phthalates, etc. and the alkyl sulfones and sulfoxides such as propyl ethyl sulfoxide, diisopropyl sulfone, diisooctyl sulfoxide, etc.

As indicated above the reaction can be suitably performmed by introducing the carbon monoxide at a desired pressure into contact with the alcoholic reaction medium containing the specified reactants, catalysts and amine salts and heating to the desired temperature. In general, a carbon monoxide pressure of about 1 to about 700 atmospheres is employed as total reaction pressure. Stoichiometric quantities of carbon monoxide are generally employed. However, an excess of carbon monoxide may be employed, for example, in continuous processes where a large excess of or high carbon monoxide requirements are generally utilized, a suitable recycle of the carbon monoxide may be employed. The reaction will proceed at temperatures of from about 50° C. to 250° C. It is generally preferred to operate the process at temperatures in the range of 100° C. to 135° C. to obtain a convenient rate of reaction. Heating and/or cooling means may be employed interior and/or exterior of the reaction to maintain the temperature within the desired range.

The reaction time is generally dependent upon the alcohol being reacted, temperature, pressure and on the amount and type of catalyst and oxidant being charged as well as the type of equipment being employed. Reaction times will vary dependent on whether the process is continuous or batch.

As indicated above, the amine salts are added to the reaction mixture in order that the reduced form of the Cu (II) oxidant salt can be readily reoxidized with oxygen or an oxygen-containing gas without the precipitation of basic copper salts and to provide a process for synthesizing oxalates in a cyclic manner. A general procedure for carrying out the process is to (1) oxidatively carbonylate the alcohol as above described, (2) remove the volatile components of the reaction products by, e.g., vacuum distillation, (3) dissolve the distillation residue in alcohol, (4) purge the resulting solution with oxygen at pressures generally greater than 0.2 atmospheres and at a temperature ranging from 20° C. to 200° C. until the Cu (I) reduced salts have been converted to the Cu (II) salts as may be determined by standard titration methods, (5) remove the reoxidation co-product water by chemical reaction by the addition of water scavengers and then distilling or by physical methods such as azeotropic distillation, (6) dilute the distillation residue with alcohol and, if necessary with amine base to insure that at least a stoichiometric quantity of the amine is present and (7) repeat the oxidative carbonylation as in (1) above. By such process it has been found that an oxidative carbonylation, utilizing the initial catalyst, amine salt and reoxidized Cu (II) oxidant can be repeated numerous times without any loss in yield of the desired oxalate ester. Without the use of the excess amine salt in the reaction the overall synthesis of oxalate esters according to the general equation,

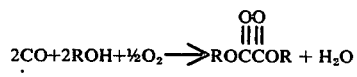

cannot be accomplished in a cyclic manner.

The water scavengers which may be used in the process of the invention include, for example, trimethyl orthoformate, trimethyl orthoacetate, triethyl orthobenzoate, 2,2-dimethoxypropane and 1,1-diethoxyethane. The water scavengers are added in a minimum of stoichiometric quantities in order to remove the contained water but except for the fact that they must be removed can also be added in larger quantities.

The solvents which may be used in the process to azeotrope off the water include, for example, solvents boiling in the range of 150° C. and above and which will entrain water such as, for example, 1,3,5-trimethylbenzene, 1,2,3,4-tetramethylbenzene, 1,2,3,4-tetramethylbenzene, o-, m- and p-xylenes and dodecane. The solvents are added in amounts sufficient to remove the contained water.

The following examples are provided to illustrate the invention in accordance with the principles of this invention but are not to be construed as limiting the invention in any way except as indicated by the appended claims.

In the runs which follow a 300 ml. stainless steel stirred autoclave was employed and the reaction products were analyzed by gas-liquid phase chromatography for the oxalate and carbonate esters.

EXAMPLE I (COMPARATIVE)

This run carried out in the absence of an excess of an amine salt shows that upon reoxidation, insoluble basic copper salts precipitated and that upon repeating the oxidative carbonylation reaction very low yield of oxalate is obtained.

Into a 300 ml. stainless steel Magnedrive autoclave is charged 1.00 g. dichlorobis (triphenylphosphine) palladium (II), 14.80 g. anhydrous copper (II) sulfate, 9.34 g. triethylamine, and 70 ml. 2-propanol. CO is pressured to 1800 psi. The temperature is raised to 125° C. for 72 minutes. The autoclave is cooled to ambient temperature, and the reaction product is recovered. The volatile components are distilled in vacuo (3 mm Hg.). The distillate contains 5.3 g. diisopropyl oxalate and 0.12 g. diisopropyl carbonate according to *glc* (gas-liquid phase chromatograph) analysis.

The residue is dissolved in 2-propanol (100 ml.) over a steam bath. A stream of oxygen is blown through the solution at a temperature of approximately 55° C. for 30 minutes. A solid Cu (II) salt precipitated immediately and would not redissolve upon addition of more 2-propanol. The solvent is removed by distillation at reduced pressure. Triethylamine is not detected in the distillate by *glc* analysis.

The residue, a dark green mushy solid, is charged to the autoclave with 70 ml. 2-propanol. The oxidative carbonylation reaction conditions is repeated as above. The reaction yields 0.62 g. diisopropyl oxalate and 0.15 g. diisopropyl carbonate according to *glc* analysis. An unusually large amount of $CO_2$ is formed in the reaction.

EXAMPLE II (COMPARATIVE)

This run demonstrates the deleterious effect water has on the carbonylation reaction. Water decreases the oxalate yield and increases the amount of $CO_2$ produced.

A mixture of 0.25 g. palladium (II) chloride, 0.75 g. triphenylphosphine, 0.83 g. water, 14.80 g. anhydrous copper (II) sulfate, 9.34 g. triethylamine, and 70 ml. 2-propanol is charged into the autoclave. The initial charge of CO is 1800 psi. The reaction temperature, 125° C., is held for 72 minutes. The autoclave is cooled to ambient temperature, and the reaction product is filtered and analyzed by *glc*. The yields of diisopropyl oxalate, diisopropyl carbonate, and $CO_2$ (in the gas phase) are respectively 1.34, 0.04, and 0.76 g.

EXAMPLE III (COMPARATIVE)

This example describes an experiment in which the additional amine salt is employed, but the water formed as a reoxidation product is not removed before the second oxidative carbonylation. The following materials are charged to the autoclave: 0.25 g. palladium (II) chloride, 0.75 g. triphenylphosphine, 9.34 g. triethylamine, 27.8 g. triethylammonium sulfate, 14.80 g. anhydrous copper (II) sulfate, and 70 ml. 2-propanol. CO is charged to 1800 psi, and the temperature raised to 125° C. for 70 minutes. The reactor is cooled to ambient temperature. According to *glc* analysis, 5.64 g. diisopropyl oxalate and 0.10 g. diisopropyl carbonate are formed. $CO_2$ is detected in the gaseous product to the extent of 0.24 g.

The volatile components of the reaction product are removed by vacuum distillation. The viscous liquid residue is dissolved in 2-propanol (100 ml.) on a steam bath. The solution is maintained at 57° C. in an oil bath while being purged with oxygen for 60 minutes. A precipitate did not form until the oxygen had been purging for 40 minutes. The solvent and amine are removed by vacuum distillation. The residue is charged along with 9.34 g. triethylamine and 2-propanol (70 ml.) to the high-pressure autoclave. The reaction conditions of the first carbonylation are repeated. The liquid reaction product contains 1.81 g. diisopropyl oxalate and 0.39 g. diisopropyl carbonate. The gaseous reaction product contains 0.31 g. $CO_2$.

EXAMPLE IV

To the high pressure autoclave is charged 0.1 g. palladium (II) iodide, 0.15 g. triphenylphosphine, 10.9 g. triethylammonium sulfate, 7.29 g. triethylamine, 11.5 g. anhydrous copper (II) sulfate, and 70 ml. 2-propanol. The autoclave is pressured to 1800 psi with CO. The temperature is raised to 125° C. for 42 minutes. The autoclave is cooled to ambient temperature. The volatile components of the reaction product are removed by vacuum distillation (3 mm Hg.). The distillate contains 4.11 g. diisopropyl oxalate and 0.10 g. diisopropyl carbonate.

The distillation residue is dissolved in 2-propanol (100 ml.). The resulting solution is purged with a stream of oxygen for 75 minutes at 55° C. After 70 minutes, a light blue solid precipitated from the dark green solution. To the reaction mixture is added 0.5 g. triethylammonium sulfate and 10.6 g. trimethyl orthoformate. The mixture is heated to reflux under nitrogen for 1 hour. All material boiling up to 82° C. (760 mm Hg.) is distilled from the product. The distillation residue is diluted with 2-propanol to 173 ml.

Triethylamine (1.3 g.) and the diluted distillation residue are charged to the autoclave. CO is charged to 1800 psi. A temperature of 125° C. is held for 33 minutes. The autoclave is cooled to ambient temperature. The liquid product, according to *glc* analysis, contains 4.25 g. diisopropyl oxalate and 0.09 g. diisopropyl carbonate. No $CO_2$ is detected in the gas product.

EXAMPLE V

To the high pressure autoclave is charged 0.27 g. copper (I) iodide, 0.74 g. triphenylphosphine, 14.80 g. copper (II) sulfate, 9.34 g. triethylamine, 13.9 g. triethylammonium sulfate, and 70 ml. 2-propanol. The autoclave is pressured to 1800 psi with CO. The temperature is raised to 135° C. for 117 minutes. The autoclave is cooled to ambient temperature. *Glc* analysis shows the presence of 3.67 g. diisopropyl oxalate and 0.13 g. diisopropyl carbonate. The gaseous product contains 0.38 g. $CO_2$.

The volatile components of the reaction product are removed by vacuum distillation (3 mm Hg.). The distillation residue is dissolved in 2-propanol (100 ml.) by heating on a steam bath. The resulting solution is purged with a stream of oxygen for 60 minutes at 55° C. A solid precipitated. This suspension is heated under reflux with 10.6 g. trimethyl orthoformate for 1 hour in a nitrogen atmosphere. All material boiling up to 82° C.

(760 mm Hg.) is distilled from the product. The distillation residue is diluted with 2-propanol to 130 ml.

The diluted distillation residue plus 1.3 g. triethylamine are charged to the autoclave. CO is charged to 1800 psi. A temperature of 135° C. is held for 60 minutes. The autoclave is cooled to ambient temperature. The liquid product according to *glc* analysis, contained 3.99 g. diisopropyl oxalate and a trace of diisopropyl carbonate. No $CO_2$ is detected in the gas product.

EXAMPLE VI

This run shows that in a palladium catalyzed oxidative carbonylation utilizing ammonium as the base, the addition of the amine salt greatly improves the yield of oxalate ester.

The following materials are charged to the high pressure autoclave: 0.51 g. palladium (II) iodide, 0.75 g. triphenylphosphine, 14.80 g. copper (II) sulfate, 6.12 g. ammonium sulfate, and 1.25 M ammonia in 2-propanol (74 ml.). 1800 psi CO is charged, and the reactor is heated to 125° C. for 146 minutes. The autoclave is cooled to ambient temperature, and the mushy reaction product in a sintered glass funnel is washed with 2-propanol. The filtrate contained 4.44 g. diisopropyl oxalate and <0.01 g. diisopropyl carbonate according to *glc* analysis. The gas product contains 0.08 g. $CO_2$.

When a similar reaction was attempted in the absence of added ammonium sulfate, the yields of diisopropyl oxalate and diisopropyl carbonate are respectively 0.16 g. and <0.01 g. $CO_2$ in the product gas analyzed is 0.14 g.

EXAMPLE VII

To the high pressure autoclave is charged 0.1 g. palladium (II) iodide, 0.1 g. lithium iodide, 4.33 g. acetic acid, 14.6 g. triethylamine, 11.5 g. anhydrous copper (II) sulfate, and 70 ml. 2-propanol. The autoclave is pressured to 1800 psi with CO. The temperature is raised to 125° C. for 60 minutes. The autoclave is cooled to ambient temperature. The reaction product contains 2.44 g. diisopropyl oxalate and 0.18 g. diisopropyl carbonate. The volatile components are removed by vacuum distillation (3 mm. Hg.).

The distillation residue is dissolved in 2-propanol (100 ml.). The solution is purged with a stream of oxygen for 3 hours at room temperature. Any material lost from the reaction mixture by the oxygen stream is trapped in a cold trap. This liquid is returned to the reaction mixture along with 12.0 g. 2,2-dimethoxypropane. The mixture is heated to reflux under nitrogen for 1 hour. All material boiling up to 82° C. (760 mm. Hg.) is distilled from the product. The distillation residue is diluted with 2-propanol to 100 ml.

The 2-propanol solution is charged to the autoclave, and the oxidative carbonylation conditions repeated. Similar yield of diisopropyl oxalate and diisopropyl carbonate is obtained.

The vacuum distillation reoxidation and dehydration steps are repeated two more times resulting in undiminished yields of diisopropyl oxalate.

EXAMPLE VIII

To the high pressure autoclave is charged 1.00 g. dichlorobis-(triphenylphosphine)-palladium (II), 14.80 g. anhydrous copper (II) sulfate, 18.68 g. triethylamine, 4.80 g. concentrated sulfuric acid, and 70 ml. absolute ethanol. The autoclave is pressured to 1800 psi with CO. The temperature is raised to 125° C., and the temperature-maintained for 65 minutes. The autoclave is cooled to ambient temperature. The reaction product determined by *glc* contains diethyl oxalate and a smaller amount of diethyl carbonate. The volatile components are removed by vacuum distillation (3 mm Hg.).

The distillation residue is dissolved in ethanol (100 ml.). The solution is purged with a stream of air for 120 minutes at 40° C. Any material vaporized from the reaction mixture by the air stream is trapped in a cold trap. This liquid is returned to the reaction mixture, which is heated under reduced pressure to remove all volatile materials (Distillate A). The residue is freed of all water of hydration by a continuous azeotropic distillation with 200 ml. mesitylene. The distillation is allowed to run overnight, after which time a quantitative amount of water has distilled over. The remaining mesitylene is removed by distillation at reduced pressure. To the residue is added the distilled volatile liquid, (Distillate A). This suspension is the charge for the next oxidative carbonylation.

The conditions of the first oxidative carbonylation are repeated. The yields of diethyl oxalate and diethyl carbonate are unchanged from the first oxidative carbonylation.

EXAMPLE IX

The conditions of Example V are reproduced but with 0.38 g. copper (II) chloride in place of copper (I) iodide. The yields of diisopropyl oxalate and diisopropyl carbonate from the first oxidative carbonylation are 3.67 g. and 0.13 g. respectively.

The conditions of the vacuum distillation, the reoxidation, and the chemical dehydration are repeated with the same results. The second oxidative carbonylation gives reproducible yields of the oxalate and carbonate esters.

EXAMPLE X

Example V is repeated but with 0.30 g. rhodium (III) chloride in place of copper (I) iodide and 70 ml. ethanol in place of 2-propanol. Triphenylphosphine is not employed. The liquid reaction product from the first oxidative carbonylation shows comparable yield of diethyl oxalate and diethyl carbonate.

The conditions of the vacuum distillation, the reoxidation, and the chemical dehydration are repeated. The second oxidative carbonylation gives reproducible yields of diethyl oxalate and diethyl carbonate.

EXAMPLE XI

A mixture of 1.00 g. dichlorobis-(triphenylphosphine)-palladium (II), 14.00 g. copper (II) oxalate, 9.34 g. triethylamine, 13.9 g. triethylammonium sulfate, and 70 ml. 2-propanol is charged into the autoclave. The CO is charged to 1800 psi. The temperature is raised to 155° C. and held for 180 minutes. Diisopropyl oxalate and a minor amount of diisopropyl carbonate is detected in the reaction product by *glc* analysis.

The conditions in Example V for the vacuum distillation, the reoxidation, and the chemical dehydration are repeated. The second oxidative carbonylation gives a reproducible yield of diisopropyl oxalate.

EXAMPLE XII

A mixture of 0.25 g. palladium (II) chloride, 0.86 g. triphenylarsine, 32.2 g. tri n-butylamine, 4.33 g. acetic acid, 14.80 g. anhydrous copper (II) sulfate, and 70 ml. t-butyl alcohol is charged to the autoclave. CO is charged to 1800 psi. The temperature is raised to 125° C. and held for 80 minutes. Di-t-butyl oxalate is detected in the reaction product by *glc* analysis.

The volatile components of the reaction product are removed by vacuum distillation. The distillation residue is dissolved in t-butyl alcohol (100 ml.) by heating on a steam bath. The resulting solution is purged with a stream of oxygen for 60 minutes at 60° C. The product is heated to the reflux temperature with 10.6 g. trimethyl orthoformate for 1 hour under nitrogen. All volatile material is removed by distillation at reduced pressure.

The residue, and 16.32 g. aniline, and 4.33 g. acetic acid were charged to the autoclave. The conditions of the first oxidative carbonylation were repeated. Di-t-butyl oxalate is detected in the liquid reaction product by *glc* analysis.

EXAMPLE XIII

The carbonylation and reoxidation of Example VIII is repeated with the exception that 13.54 g. diethylamine is used in place of triethylamine. In a second and third carbonylation similar amounts of diethyl oxalate and diethyl carbonate are obtained.

EXAMPLE XIV

The procedure of Example IV is repeated with a reaction mixture of 0.29 g. palladium (II) sulfate, 14.80 g. anhydrous copper (II) sulfate, 4.67 g. triethylamine, 10.9 g. triethylammonium sulfate, and 70 ml. absolute ethanol. The autoclave is pressurized to 1800 psi with carbon monoxide. The temperature is maintained at 130° C. for 70 minutes. The reactor is cooled to room temperature and the volatile components of the reaction product removed by vacuum distillation (3 mm Hg.). The distillate contains 1.8 g. diethyl oxalate and 0.7 g. diethyl carbonate.

The distillation residue is dissolved in ethanol (100 ml.) and the resulting solution purged with a stream of oxygen for 60 minutes at 40° C. at which time a solid precipitated. To the reaction mixture is added 10.6 g. trimethyl orthoformate and the mixture heated to reflux under nitrogen for 1 hour to remove the water and alcohol.

The distillation residue is charged to the autoclave along with 70 ml. absolute ethanol and 1.3 g. triethylamine. Carbon monoxide is charged to the autoclave to 1800 psi. The reaction temperature of 130° C. is maintained for 70 minutes. The reactor is cooled to room temperature and the reaction products analyzed by gas-liquid chromatography. Similar yields of diethyloxalate and carbonate are obtained.

EXAMPLE XV

The carbonylation-reoxidation of oxidant saltcarbonylation procedures and conditions of Example XIV are repeated with 0.63 g. palladium (II) acetate in place of the palladium (II) sulfate. The recovered products of the carbonylation reactions by *glc* analysis show significant and similar yields of diethyl oxalate and diethyl carbonate.

I claim:

1. A cyclic process for the oxidative carbonylation of an alcohol having from 1 to 20 carbon atoms which comprises the steps of reacting under substantially anhydrous conditions, a saturated monohydric aliphatic or alicyclic alcohol which may contain other substituents which do not interfere with the reaction or an aromatic alcohol selected from the group consisting of benzyl, chlorobenzyl and methoxy-benzyl alcohols with carbon monoxide at a pressure of between about 1 to 700 atmospheres and at a temperature in the range of about 50° C. to 250° C. in the presence of an effective amount of a catalyst selected from the group consisting of palladium (II), rhodium (III), platinum (II) and copper (I) or (II) salt compounds, at least a stoichiometric amount of an aliphatic, cycloaliphatic, aromatic or heterocyclic amine or ammonia, a stoichiometric quantity of a copper (II) oxalate, sulfate, acetate, or trifluroacetate oxidant salt compound, and an excess over that normally formed in the carbonylation reaction of an ammonium or substituted ammonium sulfate, acetate or trifluroacetate salt compound, to produce the desired oxalate ester;

separating the oxalate ester by distillation leaving a distillation residue comprised of catalyst, amine, reduced oxidant salt and ammonium salt compound;

dissolving the distillation residue in alcohol and purging the resulting solution with oxygen or an oxygen-containing gas at pressures above 0.2 atmospheres and at a temperature in the range of from 20° C. to 200° C. to reoxidize the reduced copper oxidant salt and form co-product water;

removing the reoxidation co-product water by the addition of water scavengers or azeotropic distillation leaving a residue comprised of catalyst, amine, copper (II) oxidant salt and ammonium salt compound; and recovering said residue for reuse in an oxidative carbonylation process.

2. A process according to claim 1 wherein the catalyst is selected from the group consisting of palladium (II) chloride, palladium (II) iodide, copper (I) iodide, copper (II) chloride, rhodium (III) chloride, palladium (II) acetate and palladium (II) sulfate.

3. A process according to claim 2 wherein the catalyst is palladium (II) chloride.

4. A process according to claim 2 wherein the catalyst is palladium (II) iodide.

5. A process according to claim 2 wherein the catalyst is copper (I) iodide.

6. A process according to claim 1 wherein the amine is selected from the group consisting of triethylamine, ammonia, tri n-butylamine and diethylamine.

7. A process according to claim 6 wherein the amine is triethylamine.

8. A process according to claim 1 wherein the copper (II) oxidant salt is copper (II) sulfate.

9. A process according to claim 1 wherein the copper (II) oxidant salt is copper (II) oxalate.

10. A process according to claim 1 wherein the reaction is carried out in the presence of a co-catalytic amount of an organic mono- or poly-dentate ligand selected from the group consisting of alkyl, aryl and halogen substituted phosphines, arsines, stibines and iodides.

11. A process according to claim 10 wherein the ligand is selected from the group consisting of triethylphosphine, triphenylphosine, triphenylarsine and lithium iodide.

12. A process according to claim 1 wherein the alcohol is selected from the group consisting of ethyl alcohol, isopropyl alcohol and tert-butyl alcohol.

13. A process according to claim 12 wherein the alcohol is isopropyl alcohol.

14. A process according to claim 1 wherein the pressure is between about 100 and 200 atmospheres and the temperature is in the range of about 100° C. to 135° C.

15. A process according to claim 1 wherein the ammonium or substituted ammonium salt compound is selected from the group consisting of triethyl ammonium sulfate, ammonium sulfate and triethyl ammonium acetate.

16. A process according to claim 15 wherein the ammonium salt compound is triethylammonium sulfate.

17. A process according to claim 1 wherein the ammonium salt or substituted ammonium salt compounds are employed in molar concentrations or from about 0.25 to 2 moles of said salt based on stoichiometric amount of amine.

18. A process according to claim 1 wherein the ammonium salt or substituted ammonium salt is formed in situ upon the addition of an acid.

19. A process according to claim 18 wherein said acid is sulfuric acid.

20. A process according to claim 18 wherein the acid is acetic acid.

21. A process according to claim 1 wherein the alcohol is isopropyl alcohol, the catalyst is palladium (II) iodide, the amine is triethylamine, the oxidant salt is copper (II) sulfate and the substituted ammonium sait is triethylammonium sulfate.

22. A process according to claim 1 wherein the alcohol is isopropyl alcohol, the catalyst is copper (I) iodide, the amine is triethylamine, the oxidant salt is copper (II) sulfate and the substituted ammonium salt is triethylammonium sulfate.

* * * * *